United States Patent [19]

Schiller

[11] Patent Number: 5,455,230
[45] Date of Patent: Oct. 3, 1995

[54] DELTA OPIOID RECEPTOR ANTAGONISTS AND THEIR USE AS ANALGESIC AGENTS

[75] Inventor: Peter W. Schiller, Montreal, Canada

[73] Assignee: Aktiebolaget Astra, Sodertalje, Sweden

[21] Appl. No.: 21,773

[22] Filed: Feb. 24, 1993

[51] Int. Cl.$^6$ .................................................. A61K 38/07
[52] U.S. Cl. ........................... 514/18; 530/330; 530/331; 562/444
[58] Field of Search ........................ 514/17–18; 530/330

[56] References Cited

PUBLICATIONS

Schiller *Proc Natl Acad Sci* 89 11871 1992.
The FASEB Journal 6, A1575 (1992), 3699, [published Feb. 26, 1992].
JASPEC '92 Abstract Form.
Journal of Medicinal Chemistry, vol. 31, p. 281 1988.
Journal of Medicinal Chemistry, vol. 34, p. 1757 1991.
European Journal of Pharmacology, 97 (1984) 331–332.

*Primary Examiner*—Jill Warden
*Assistant Examiner*—David Lukton
*Attorney, Agent, or Firm*—White & Case

[57] ABSTRACT

Compounds of the formula I as well as a process for their preparation, their pharmaceutical preparations and their use H—Tyr—Tic—X   (I)

wherein X is
—Phe—OH,
—Phe—NH$_2$,
—Phe—Phe—OH,
—Phe—Phe—NH$_2$,
—Trp—Phe—NH$_2$,
—Trp—Phe—OH,
—Phe—Phe(p-NO$_2$)—OH,
—Trp—Phe(p-NO$_2$)—H or
—Phe—Trp—NH$_2$

12 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="N,N-diallyltyrosine"

( i x ) FEATURE:
        ( A ) NAME/KEY: Modified-site
        ( B ) LOCATION: 2
        ( D ) OTHER INFORMATION: /label=Aib
            / note="alpha-aminoisobutyric acid"

( i x ) FEATURE:
        ( A ) NAME/KEY: Modified-site
        ( B ) LOCATION: 3
        ( D ) OTHER INFORMATION: /label=Aib
            / note="alpha-aminoisobutyric acid"

( x i ) SEQUENCE DESCRIPTION: SEQ ID NO:1:

Xaa  Xaa  Xaa  Phe  Leu
    1                         5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide -continued

```
    ( i x ) FEATURE:
              ( A ) NAME/KEY: Modified-site
              ( B ) LOCATION: 2
              ( D ) OTHER INFORMATION: /label=Tic
                        / note=
                        " 1,2,3,4-tetrahydroisoquinoline-3-carboxylic acid"

( x i ) SEQUENCE DESCRIPTION: SEQ ID NO:2:

Tyr  Xaa  Phe  Phe
    1

( 2 ) INFORMATION FOR SEQ ID NO:3:

( i ) SEQUENCE CHARACTERISTICS:
              ( A ) LENGTH: 4 amino acids
              ( B ) TYPE: amino acid
              ( D ) TOPOLOGY: linear ( i i ) MOLECULE TYPE: peptide ( i x ) FEATURE:
              ( A ) NAME/KEY: Modified-site
              ( B ) LOCATION: 2
              ( D ) OTHER INFORMATION: /label=Tic
                        / note=
                        " 1,2,3,4-tetrahydroisoquinoline-3-carboxylic acid"

( i x ) FEATURE:
              ( A ) NAME/KEY: Modified-site
              ( B ) LOCATION: 4
              ( D ) OTHER INFORMATION: /note="Phe-NH2 (phenylalanine
                        amide)"

( x i ) SEQUENCE DESCRIPTION: SEQ ID NO:3:

Tyr  Xaa  Phe  Xaa
    1

( 2 ) INFORMATION FOR SEQ ID NO:4:

( i ) SEQUENCE CHARACTERISTICS:
              ( A ) LENGTH: 4 amino acids
              ( B ) TYPE: amino acid
              ( D ) TOPOLOGY: linear ( i i ) MOLECULE TYPE: peptide ( i x ) FEATURE:
              ( A ) NAME/KEY: Modified-site
              ( B ) LOCATION: 2
              ( D ) OTHER INFORMATION: /label=Tic
                        / note=
                        " 1,2,3,4-tetrahydroisoquinoline-3-carboxylic acid"

( i x ) FEATURE:
              ( A ) NAME/KEY: Modified-site
              ( B ) LOCATION: 4
              ( D ) OTHER INFORMATION: /note="Phe-NH2 (phenylalanine
                        amide)"

( x i ) SEQUENCE DESCRIPTION: SEQ ID NO:4:

Tyr  Xaa  Trp  Xaa
    1

( 2 ) INFORMATION FOR SEQ ID NO:5:

( i ) SEQUENCE CHARACTERISTICS:
              ( A ) LENGTH: 4 amino acids
              ( B ) TYPE: amino acid
              ( D ) TOPOLOGY: linear ( i i ) MOLECULE TYPE: peptide ( i x ) FEATURE:
```

( A ) NAME/KEY: Modified-site
( B ) LOCATION: 2
( D ) OTHER INFORMATION: /label=Tic
/ note=
" 1,2,3,4-tetrahydroisoquinoline-3-carboxylic acid"

( x i ) SEQUENCE DESCRIPTION: SEQ ID NO:5:

Tyr  Xaa  Trp  Phe
1

( 2 ) INFORMATION FOR SEQ ID NO:6:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /label=Tic
/ note=
" 1,2,3,4-tetrahydroisoquinoline-3-carboxylic acid"

( i x ) FEATURE:
( A ) NAME/KEY: Modified-site
( B ) LOCATION: 4
( D ) OTHER INFORMATION: /note="Phe(p-NO2)-OH (para-nitro
phenylalanine)"

( x i ) SEQUENCE DESCRIPTION: SEQ ID NO:6:

Tyr  Xaa  Phe  Xaa
1

( 2 ) INFORMATION FOR SEQ ID NO:7:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /label=Tic
/ note=
" 1,2,3,4-tetrahydroisoquinoline-3-carboxylic acid"

( i x ) FEATURE:
( A ) NAME/KEY: Modified-site
( B ) LOCATION: 4
( D ) OTHER INFORMATION: /note="Phe(p-NO2)-OH (para-nitro
phenylalanine)"

( x i ) SEQUENCE DESCRIPTION: SEQ ID NO:7:

Tyr  Xaa  Trp  Xaa
1

( 2 ) INFORMATION FOR SEQ ID NO:8:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Modified-site (B) LOCATION: 2
(D) OTHER INFORMATION: /label=Tic
/ note=
"1,2,3,4-tetrahydroisoquinoline-3-carboxylic acid"

(ix) FEATURE:
(A) NAME/KEY: Modified-site
(B) LOCATION: 4
(D) OTHER INFORMATION: /note="Trp-NH2 (tryptophan amide)"

(xi) SEQUENCE DESCRIPTION: SEQ ID NO:8:

Tyr Xaa Phe Xaa
1

DELTA OPIOID RECEPTOR ANTAGONISTS AND THEIR USE AS ANALGESIC AGENTS

THE FIELD OF THE INVENTION

This invention is related to a new class of opioid peptide analogs that are δ opioid receptor antagonists as well as to their synthesis and their use as analgesic and immunosuppressive compounds.

BACKGROUND

A known nonpeptide δ opioid antagonist is naltrindole, which is described by P. S Portoghese, et al J. Med Chem 31, 281–282 (1988). Naltrindole has similar δ antagonist potency as the compounds according to this invention but is much less δ selective. Furthermore, naltrindole has also quite high p opioid receptor affinity ($K_i^\mu$=12 nM) in the receptor binding assay and potent antagonist properties ($K_e$=29 nM) in the guinea pig ileum (GPI) assay, cf P. S Portoghese, J. Med. Chem, 34, 1757–1762 (1991).

Another known δ-antagonist is the enkephalin analog N,N—diallyl—Tyr—Aib—Aib—Phe—Leu—OH (ICI 174864) (SEQ ID NO:1 in the Sequence Listing) described by R. Cotton, et al in Eur. J. Pharmacol, 97, 331–332 (1984). In comparision with the most potent and selective δ antagonists described in this patent application, ICI 174864 is much less δ-selective (40 times less) and has much lower antagonist potency in the MVD assay (20 times less potent).

THE INVENTION

It has now unexpectedly been found that the compounds of the following formula I have
extraordinary selectively for the δ receptor
high potency as δ antagonists
total lack of μ antagonist properties
possibility to "build in" an additional μ opioid agonist component to develop mixed μ agonists/δ antagonists.

The compounds according to the present invention have the formula I

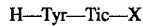   (I)

wherein X is
—Phe—OH
—Phe—NH$_2$
—Phe—Phe—OH
—Phe—Phe—NH$_2$
—Trp—Phe—NH$_2$,
—Trp—Phe—OH,
—Phe—Phe(p-NO$_2$)—OH
—Trp—Phe(p-NO$_2$)—OH or
—Phe—Trp—NH$_2$.

Thus one of the following compounds:
H—Tyr—Tic—Phe—OH (TIP)
H—Tyr—Tic—Phe—NH$_2$(TIP—NH$_2$)
H—Tyr—Tic—Phe—Phe—OH (TIPP)
H—Tyr—Tic—Phe—Phe—NH$_2$(TIPP—NH$_2$)
H—Tyr—Tic—Trp—Phe—NH$_2$
H—Tyr—Tic—Trp—Phe—OH
H—Tyr—Tic—Phe—Phe(p-NO$_2$)—OH
H—Tyr—Tic—Trp—Phe(p-NO$_2$)—OH
H—Tyr—Tic—Phe—Trp—NH$_2$
wherein H—Tyr—Tic—Phe—Phe—OH(TIPP) is SEQ ID NO:2, H—Tyr—Tic—Phe—Phe—NH$_2$(TIPP—NH$_2$) is SEQ ID NO:3, H—Tyr—Tic—Trp—Phe—NH$_2$ is SEQ ID NO:4, H— Tyr—Tic—Trp—Phe—OH is SEQ ID NO:5, H—Tyr—Tic—Phe—Phe(p-NO$_2$)—OH is SEQ ID NO:6, H—Tyr—Tic—Trp—Phe(p-NO$_2$)—OH is SEQ ID NO:7 and H—Tyr—Tic—Phe—Trp—NH$_2$ is SEQ ID NO:8 in the Sequence Listing.

SYNTHESIS

The Boc-amino acid derivatives used in the peptide syntheses were commercially available. All peptides were prepared by solid-phase techniques. The usual polystyrene/divinylbenzene resin was used for the solid-phase synthesis of peptides with a free-C-terminal carboxyl group, whereas peptide amides were synthesized by using the p-methylbenzhydrylamine resin. Boc protection of the amino group was employed in the preparation of all peptides. The syntheses were performed according to protocols that have been extensively used in the inventor's laboratory (P. W Schiller et at, Biochemisty 16, 1831–1838 (1977). Couplings were performed in CH$_2$Cl$_2$ or DMF, using dicyclohexylcarbodi-imide/1-hydroxybenzotriazole (DCC/HOBt) as coupling agents. Completeness of coupling was carefully examined after each coupling step by means of the ninhydrin color test. The fully assembled peptide chain was cleaved from the resin and completely deprotected by treatment with liquid HF at 0° C. and in the presence of anisole as scavenger (60–90 min).

Crude products obtained from solid-phase peptide synthesis required extensive purification by various chromatographic techniques or by other methods. Following HF cleavage and extraction of the resin gel filtration on Sephadex (G-15 or G-25) were routinely performed. Various subsequent purification steps included partition chromatography on Sephadex G-25 (using various butanol-acetic acid-pyridine-water two phase systems), ion exchange chromatography (DEAE-Sephadex, SP-Sephadex and CM-cellulose) and reversed-phase chromatography on an octadecasilyl-silica column using linear gradients of methanol in 1% trifluoroacetic acid (low pressure). If necessary, final purification to homogeneity was performed by semi-preparative HPLC. Semi-preparative μ-Bondapak C-18 columns (Waters; 0.7×25 cm), which, depending on the separation problem, permitted purification of 2–20 mg peptide material per run were used. Several highly sensitive and efficient analytical methods were used to demonstrate homogeneity of the prepared peptides and to verify their structures. Thin layer chromatography in at least two different solvent systems was used to establish purity. Furthermore, analytical HPLC in two or three different solvent systems was routinely used in the laboratory as a highly sensitive purity test. Verification of peptide structures was mainly based on amino acid analysis and fast atom bombardment-mass spectrometry (FAB-MS): For amino acid analyses, peptides were hydrolyzed in 6N HCl containing a small amount of phenol for 24 h at 110° C. in deaerated tubes (in some cases hydrolyses lasting for 12 and 48 h were also performed to take into account amino acid degradation). Hydrolysates were analyzed on a Beckman Model 121 C amino acid analyzer equipped with a system AA computing integrator. FAB mass spectrometry was used to establish the correct molecular weights of the peptides.

EXAMPLES OF PARTICULAR ANALOGS

EXAMPLE 1

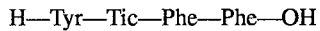

Boc—Phe—O—resin (1 g, 0.61 mmol Boc—Phe/g resin; Peninsula, Belmont, Calif.) was washed with reagents in the following sequence: CH$_2$Cl$_2$ (3×1 min), 50% (v/v) TFA in CH$_2$Cl$_2$ (30 min), CH$_2$Cl$_2$ (5×1 min), 10% v/v DIEA in $CH_2Cl_2$ (2×5 min), $CH_2Cl_2$ (5×1 min). Boc—Phe—OH (404 mg, 1.52 mmol) was then coupled using HOBt (205 mg, 1.52 mmol) and DCC (313 mg, 1.52 mmol) in $CH_2Cl_2$/DMF (3:1, v/v) for 17 h. The resin was then washed with $CH_2Cl_2$ (3×1 min), EtOH (1 min), $CH_2Cl_2$ (3×1 min). This sequence of washings and reactions was repeated for the addition of each of the residues with the following modifications. After coupling of Boc—Tic—OH the resin was washed with $CH_2Cl_2$/DMF (3:1, v/v) (3 ×) and a recoupling step using the same amounts of Boc—Tic—OH, HOBt and DCC in $CH_2Cl_2$/DMF (3:1, v/v) was performed for another 17h. The same recoupling step was also carried out to couple Boc—Tyr(Boc)—OH.

After final deprotection with 50% (v/v) TFA in $CH_2Cl_2$ (30 min), the resin was washed with $CH_2Cl_2$ (3×1 min) and EtOH (3×1 min) and was dried in a desiccator. The dry resin was treated with 20 ml of HF plus 1 ml of anisole first for 90 min at 0° C. and then for 15 min at room temperature. After evaporation of the HF, the resin was extracted three times with $Et_2O$ and, subsequently three times with 7% AcOH. The crude peptide was then obtained in solid form through lyophilization of the combined acetic acid extracts.

The peptide was purified by gel filtration on a Sephadex-G-25 column in 0.5N AcOH followed by reversed-phase chromatography on an octadecasilyl silica column with a linear gradient of 0–80% MeOH in 1% TFA. After solvent evaporation the pure peptide was dissolved in conc. AcOH and was obtained in solid form through lyophilization.

Yield: 52 mg

FAB-MS: $MH^+=635$

TLC (silica) Rf 0.77 n-BuOH/AcOH/$H_2O$ (4/1/5, organic phase)

Rf 0.79 n-BuOH/Pyridine/AcOH/$H_2O$ (15/10/3/12)

Amino acid analysis: Tyr 0.95, Phe 2.00

EXAMPLE 2

H—Tyr—Tic—Phe—Phe—$NH_2$ p-Methylbenzhydrylamine resin (1 g, 0.69 mmol/g of titratable amin; Peninsula, Belmont, Calif.) was washed with reagents in the following sequence: $CH_2Cl_2$ (3×1 min), 10% v/v DIEA in $CH_2Cl_2$ (2×5 min), $CH_2Cl_2$ (5×1 min). Boc—Phe—OH (458 mg, 1.72 mmol) was then coupled using HOBt (232 mg, 1.72 mmol) and DCC (354 mg, 1.72 mmol) in $CH_2Cl_2$/DMF (3:1, v/v) for 17 h. The resin was then washed with $CH_2Cl_2$ (3×1 min), EtOH (1 min), $CH_2Cl_2$ (3×1 min) and deprotected with 50% (v/v) TFA in $CH_2Cl_2$. This sequence of washings and reactions was repeated for the addition or each of the residues. As in the case of EXAMPLE 1, a recoupling step was performed for linking Boc—Tic—OH and Boc—Tyr(Boc)—OH. The peptide was cleaved from the resin, purified and lyophilized as described in EXAMPLE 1.

Yield: 65 mg

FAB-MS: $MH^+=634$

TLC (silica) Rf 0.75 n-BuOH/AcOH/$H_2O$ (4/1/5, organic phase)

Rf 0.81 n-BuOH/Pyridine/AcOH/$H_2O$ (15/10/3/12)

Amino acid analysis: Tyr 0.97, Phe 2.00

Pharmacological testing in vitro of δ opioid antagonists

Biosassys based on inhibition of electrically evoked contractions of the mouse vas deferens (MVD) and of the guinea pig ileum (GPI). In the GPI assay the opioid effect is primarily mediated by μ opioid receptors, whereas in the MVD assay the inhibition of the contractions is mostly due to interaction with δ opioid receptors. Antagonist potencies in these assays are expressed as so-called $K_e$-values (H. W Kosterlitz & A. J Watt, Br. J. Pharmacol. 33, 266–276 (1968)). Agonist potencies are expressed as IC50 values (concentration of the agonist that produces 50% inhibition of the electrically induced contractions).

Bioassays Using Isolated Organ Preparations

The GPI and MVD bioassays were carried out as reported in P. W. Schiller et al Biochem. Biophys. Res. Commun 85, 1332–1338 (1978) and J. DiMaio et al, J. Med. Chem 25 1432–1438 (1982). A log dose-response curve was determind with [$Leu^5$]enkephalin as standard for each ileum and vas preparation, and IC50 values of the compounds being tested were normalized according to A. A Waterfield et al Eur. J. Pharmacod 58, 11–18 (1979). $K_e$ values for the TIPP-related antagonists were determind from the ratio of IC50 values (DR) obtained in the presence and absence of a fixed antagonist concentration (a) ($K_e$=a/(DR-1 ) H. W. Kosterlitz & A. J. Watt, Br. J. Pharmacol. 33, 266–276 (1968). These determinations were made with the MVD assay, using three different δ -selective agonists ([$Leu^5$] enkephalin, DPDPE and [D-$Ala^2$]deltorphin I.

In the following Table 1 the results are given.

TABLE 1

$K_e$-values of TIP(P) related peptides in the MVD assay (Antagonist potencies against the δ agonists [$Lue^5$]enkephalin [D-$Pen^2$, D-$Pen^5$] enkephalin (DPDPE) 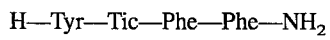 and [D-$Ala^2$]deltorphin I)

$K_e$ (nM)[a]

| Compound | [$Leu^5$]-Enkephalin | DPDPE | [D-$Ala^2$]-deltorphin I |
|---|---|---|---|
| H—Tyr—Tic—Phe—OH | 11.7 ± 1.8 | 16.1 ± 1.9 | 12.6 ± 1.8 |
| H—Tyr—Tic—Phe—$NH_2$ | 43.9 ± 8.9 | 96.8 ± 14.1 | 58.9 ± 7.7 |
| H—Tyr—Tic—Phe—Phe—OH | 5.86 ± 0.33 | 4.80 ± 0.20 | 2.96 ± 0.02 |
| H—Tyr—Tic—Phe—Phe—$NH_2$ | 15.7 ± 2.4 | 18.0 ± 2.0 | 14.4 ± 2.2 |
| H—Tyr—Tic—Trp—Phe—OH | 2.37 ± 0.54 | 2.56 ± 0.21 | 1.65 ± 0.18 |
| H—Tyr—Tic—Trp—Phe—$NH_2$ | 3.24 ± 0.43 | 4.65 ± 0.92 | 2.31 ± 0.17 |
| H—Tyr—Tic—Phe—Phe(p-$NO_2$)—OH | 3.62 ± 0.46 | 3.30 ± 0.35 | 2.79 ± 0.46 |
| H—Tyr—Tic—Trp—Phe(p-$NO_2$)—OH | 1.83 ± 0.10 | 4.40 ± 0.55 | 2.27 ± 0.14 |

TABLE 1-continued $K_e$-values of TIP(P) related peptides in the MVD assay (Antagonist potencies against the δ agonists [Leu⁵]enkephalin [D-Pen², D-Pen⁵] enkephalin (DPDPE) and [D-Ala²]deltorphin I)

$K_e$ (nM)ᵃ

| Compound | [Leu⁵]-Enkephalin | DPDPE | [D-Ala²]-deltorphin I |
|---|---|---|---|
| H—Tyr—Tic—Phe—Trp—NH₂ | 49.5 ± 4.6 | 41.3 ± 5.2 | 38.6 ± 3.3 |
| Naltrindole | 0.850 ± 0.221 | 0.634 ± 0.161 | 0.636 ± 0.105 |

-end of table 1-
ᵃValues are means of 3–8 determinations ± SEM

CONCLUSION

μ Antagonist or μ Agonist behavior of the δ antagonists

All compounds show no μ antagonist activity in the GPI assay at concentrations as high as 10 μM.

TIPP-related peptides with a free C-terminal carboxyl group have very weak μ agonist potency in the GPI assay (IC50>10 pM). On the other hand, TIPP-related peptides with a C-terminal carboxamide function show moderate μ agonist potency in the GPI assay (e.g. H—Tyr—Tic—Phe—Phe—NH₂ (TIPP—NH₂) has an IC50 of 1700±220 nM in the GPI assay.

Opioid receptor binding assays

μ and δ opioid receptor binding constants ($K_i^\mu$, $K_i^\delta$) of the compounds were determind by displacement of relatively selective μ and δ radioligands from binding sites in rat brain membrane preparations (calculated from the measured IC50 values on the basis of the equation by Cheng & Prusoff (Y. C. Cheng and W. H. Prusoff (Biochem. Pharmacol. 22, 3099–3102 (1973)).

In the following Table 2 the results of the opioid receptor binding assays are given. The ratio $K_i^\mu/K_i^\delta$ is a quantitative measure of the δ-selectivity. The higher the ratio the better the δ-selectivity.

Opioid receptor binding studies

The μ-, δ- and κ-opioid receptor affinities of all new analogs were determind in binding assays based on displacement of μ-, δ- and κ-selective radioligands from rat brain membrane binding sites. In the case of κ-ligands guinea pig brain homogenates were used, since the relative proportion of κ-binding sites is higher in guinea pig brain than in rat brain. The experimental procedure being used in our laboratory represents a modified version of the binding assay described by Pasternak et al. (Mol. Pharmacol. 11,340–351, (1975)). Male Sprague-Dawley rats (300–350 g) from the Canadian Breeding Laboratories were decapitated and after removal of the cerebellum the brains were homogenized in 30 volumes of ice-cold standard buffer (50 mM Tris-HCl, pH 7.7). After centrifugation at 30,000×g for 30 min at 4° C. the membranes were reconstituted in the original volume of standard buffer and incubated for 30 min at 37° C. (to release bound endogenous ligands). Subsequent centrifugation and resuspension of the pellet in the initial volume of fresh standard buffer yielded the final membrane suspension. Aliquots (2 ml) of the membrane preparations were incubated for 1–2 h at 25° C. with 1 ml standard buffer containing the peptide to be tested and one of the following radioligands at the final concentration indicated: [³H] DAMGO, μ-selective, 0.7 nM; [³H]DSLET, [³H]DPDPE, or [³H]TIPP, δ-selective, 1.0 nM; and [³H]U69,563, κ-selective, 0.5 nM. The incubation was terminated by filtration through Whatman GF/B filters under vacuum at 4° C. Following two washings with 5 ml portions of ice-cold standard buffer the filters were transferred to scintillation vials and treated with 1 ml Protosol (New England Nuclear) for 30 min prior to the addition of 0.5 ml acetic acid and 10 ml Aquasol (New England Nuclear). After shaking for 30 min the vials were counted at an efficiency of 40–45%. All experiments were performed in duplicates and repeated at least three times. Specific binding of each of the three radioligands was defined by performing incubations in the presence of cold DAGO, DSLET and U69,563, respectively, at a concentration of 1 micromolar. Values of half-maximal inhibition (IC50) of specific binding were obtained graphically from semilogarithmic plots. From the measure IC50-values, binding inhibition contants ($K_i$) were then calculated based on Cheng and Prusoff's equation (Biochem. Pharmcol. 22, 3099-3102 (1973). Ratios of the $K_i$-values in the μ, δ- and κ- representative binding assays are a measure of the receptor selectivety of the compound under investigation (e.g. $K_i^\mu/K_i^\delta$ indicates the selectivity for δ-receptors versus μ-receptors). None of the compounds according to the claimed invention had significant affinity for κ-receptors.

TABLE 2

Receptor binding data of opioid peptide analogsᵃ

| Compound | $K_i^\mu$ [nM] | $K_i^\delta$ [nM] | $K_i^\mu/K_i^\delta$ |
|---|---|---|---|
| H—Tyr—Tic—Phe—OH | 1280 ± 140 | 9.07 ± 1.02 | 141 |
| H—Tyr—Tic—Phe—NH₂ | 624 ± 79 | 12.0 ± 1.3 | 52.0 |
| H—Tyr—Tic—Phe—Phe—OH | 1720 ± 50 | 1.22 ± 0.07 | 1410 |
| H—Tyr—Tic—Phe—Phe—NH₂ | 78.8 ± 7.1 | 3.00 ± 0.15 | 26.3 |
| H—Tyr—Tic—Trp—Phe—NH₂ | 176 ± 21 | 0.248 ± 0.009 | 709 |
| H—Tyr—Tic—Trp—Phe—OH | 1790 ± 380 | 0.301 ± 0.042 | 5950 |
| H—Tyr—Tic—Phe—Phe(p-NO₂)—OH | 2890 ± 660 | 0.703 ± 0.099 | 4110 |
| H—Tyr—Tic—Trp—Phe(p-NO₂)—OH | 1520 ± 42 | 0.330 ± 0.004 | 4610 |
| H—Tyr—Tic—Phe—Trp—NH₂ | 312 ± 75 | 1.21 ± 0.19 | 258 |
| Naltrindole | 12.2 ± 1.9 | 0.687 ± 0.100 | 17.8 |

-end of table 2-
ᵃValues are means of 3 determinations ± SEM

Potential use

The pure δ antagonists may be used in combination with analgesics of the μ agonist type (e.g. morphine) to prevent the development of tolerance and dependence, as suggested by the results of E. E. Abdelhamid et al J. Parmacol. Exp. Ther. 258, 299–303 (1991). The latter study also suggested that compounds with mixed μ agonist/δ antagonist properties may be therapeutically useful as analgesics that do not produce tolerance and dependence. The TIPP-related compounds with a C-terminal carboxamide group described in this patent are the first mixed μ agonists/δ antagonists known.

The δ antagonists described in the patent may also be therapeutically useful as immunosuppressive agents. Immunosuppressive effects of the less δ-selective and less "pure" δ antagonist naltrindole have been described by K. Arakawa et al. Transplantation Proc. 24, 696–697 (1992); Transplantation 53, 951–953 (1992).

The best mode according to the invention known at present is the compound H—Tyr—Tic—Trp—Phe—OH because of its superior δ antagonist potency and δ selectivity.

| Abbreviations |
|---|
| Aib = α-aminoisobutyric acid |
| Boc = tert-butoxycarbonyl |
| DAMGO = H—Tyr-D-Ala—Gly—Phe($N^\alpha$Me)—Gly-ol |
| DCC = dicyclohexylcarbodiimide |
| DUEA = diisopropylethylamine |
| DPDPE = [D-Pen$^2$, D-Pen$^5$]enkephalin |
| DSLET = H—Tyr-D-Ser—Gly—Phe—Leu—Thr—OH |
| FAB-MS = fast atom bombardment mass spectrometry |
| GPI = guinea pig ileum |
| HOBt = 1-hydroxybenzotriazole |
| MVD = mouse vas deferens |
| Phe(p-$NO_2$) = 4-nitrophenylalanine |
| Tic = 1,2,3,4-tetrahydroisoquinoline-3-carboxylic acid |
| TIP = H—Tyr—Tic—Phe—OH |
| TIP—$NH_2$ = H—Tyr—Tic—Phe—$NH_2$ |
| TIPP = H—Tyr—Tic—Phe—Phe—OH |
| TIPP—$NH_2$ = H—Tyr—Tic—Phe—Phe—$NH_2$ |
| U69,593 = (5α, 7α, 8β)-(−)-N-methyl-[7-(1-pyrrolidinyl)-1-oxaspiro[4.5]dec-8-yl]benzeneacetamide |

I claim:

1. A compound of the formula I
H—Tyr—Tic—X
wherein X is
—Phe—OH,
—Phe—NH$_2$,
—Phe—Phe—OH,
—Phe—Phe—NH$_2$,
—Trp—Phe—NH$_2$,
—Trp—Phe—OH,
—Phe—Phe(p—NO$_2$)—OH,
—Trp—Phe(p-NO$_2$)—OH or
—Phe—Trp—NH$_2$.

2. A compound according to formula I of claim 1, namely H—Tyr—Tic—Phe—OH.

3. A compound according to formula I of claim 1, namely H—Tyr—Tic—Phe—NH$_2$.

4. The compound according to formula I of claim 1 which is H—Tyr—Tic—Phe—Phe—OH (SEQ ID NO:2 in the Sequence Listing).

5. The compound according to formula I of claim 1 which is H—Tyr—Tic—Phe—Phe—NH$_2$ (SEQ ID NO:3 in the Sequence Listing).

6. The compound according to formula I of claim 1 which is H—Tyr—Tic—Trp—Phe—NH$_2$ (SEQ ID NO:4 in the Sequence Listing).

7. The compound according to formula I of claim 1 which is H—Tyr—Tic—Trp—Phe—OH (SEQ ID NO:5 in the Sequence Listing).

8. The compound according to formula I of claim 1 which is H—Tyr—Tic—Phe—Phe(p-NO$_2$)—OH (SEQ ID NO:6 in the Sequence Listing).

9. The compound according to formula I of claim 1 which is H—Tyr—Tic—Trp—Phe(p-NO$_2$)—OH SEQ ID NO:7 in the Sequence Listing).

10. The compound according to formula I of claim 1 which is H—Tyr—Tic—Phe—Trp—NH$_2$ (SEQ ID NO:8 in the Sequence Listing).

11. A pharmaceutical preparation comprising an effective amount of a compound according to claim 1 together with one or more pharmaceutical carriers.

12. A method for providing analgesia to a patient which comprises administering to the patient a pharmaceutically effective amount of a compound according to claim 1.

* * * * *